(12) United States Patent
Satake (10) Patent No.: US 6,952,615 B2
(45) Date of Patent: Oct. 4, 2005

(54) RADIOFREQUENCY THERMAL BALLOON CATHETER

(76) Inventor: Shutaro Satake, 4-8-18, Kamakurayama, Kamakura-Shi, Kanagawa-Ken (JP)

( * ) Notice: Subject to any disclaimer, the term of this patent is extended or adjusted under 35 U.S.C. 154(b) by 537 days.

(21) Appl. No.: 10/173,107

(22) Filed: Jun. 18, 2002

(65) Prior Publication Data

US 2003/0065371 A1 Apr. 3, 2003

(30) Foreign Application Priority Data

Sep. 28, 2001 (JP) .................................... 2001-303112

(51) Int. Cl.⁷ ................................................ A61F 2/00
(52) U.S. Cl. .................... 607/102; 604/96.01; 604/113
(58) Field of Search ............................ 604/96.01, 113, 604/114, 20, 21; 607/102; 606/41, 28–31

(56) References Cited

U.S. PATENT DOCUMENTS

| | | | | |
|---|---|---|---|---|
| 4,160,455 A | * | 7/1979 | Law ........................... | 607/105 |
| 5,344,398 A | | 9/1994 | Hara | |
| 5,578,008 A | | 11/1996 | Hara | |
| 5,743,900 A | | 4/1998 | Hara | |
| 2002/0029062 A1 | * | 3/2002 | Satake ........................ | 606/194 |
| 2004/0147915 A1 | * | 7/2004 | Hasebe ........................ | 606/28 |
| 2004/0172110 A1 | * | 9/2004 | Satake ........................ | 607/101 |

FOREIGN PATENT DOCUMENTS

| | | | |
|---|---|---|---|
| JP | 2510428 | | 4/1996 |
| JP | 2001-503666 | | 3/2001 |
| WO | WO 96/15741 | * | 5/1996 |
| WO | 98/22032 | | 5/1998 |

* cited by examiner

Primary Examiner—Sharon Kennedy
(74) Attorney, Agent, or Firm—Wenderoth, Lind & Ponack, L.L.P.

(57) ABSTRACT

A radiofrequency thermal balloon catheter uniformly heats tissues in contact with the balloon to achieve thermotherapy such as ablation or hyperthermia safely and properly for a diseased part. The radiofrequency thermal balloon catheter includes a catheter (4) having an outer shaft (2) and an inner shaft 3 extended through the outer shaft so as to be slidable relative to the outer shaft, an inflatable balloon (6) capable of being inflated so as to be in contact with a target lesion (18) and provided between respective front end parts of the outer and the inner shaft, and a radiofrequency electrode (8) extended in a wall of the balloon or inside the balloon to be used for radiofrequency energy supply in combination with a counter electrode (53). The counter electrode is disposed at a predetermined position, for example, inside the balloon, in the wall of the balloon, in a position neighboring the balloon or on the patient's body surface. A lead wire (10) electrically connects to the radiofrequency electrode. A temperature sensor (12) is capable of sensing temperature of a liquid contained in the balloon. A temperature distribution uniformizing device (14) uniformizes the temperature distribution in the liquid contained in the balloon.

15 Claims, 8 Drawing Sheets

RADIOFREQUENCY THERMAL BALLOON CATHETER

BACKRGROUND OF THE INVENTION

1. Field of the Invention

The present invention relates to a radiofrequency thermal balloon catheter (RTBC) and, more particularly, to a radiofrequency thermal balloon catheter for the treatment of cardiovascular disease.

2. Description of the Related Art

Therapeutic methods using an inflatable balloon, and an electrode placed in the balloon, and capable of creating a radiofrequency electric field by supplying radiofrequency energy to the electrode to heat the tissues in contact with the balloon for therapy, are disclosed in, for example, Japanese Patent Nos., 2538375, 2510428 and 2574119 granted to the applicant of the present invention. The tissues in contact with the balloon must be uniformly or homogeneously heated to achieve the therapy satisfactorily. However, electrode lines forming the electrode cannot be uniformly arranged in the balloon. If the lines of the electrode are irregularly arranged, a liquid contained in the balloon is irregularly or inhomogeneously heated. The local temperature difference of the liquid contained in the balloon also increases due to convection and the temperature of the upper part in the balloon becomes higher. Consequently, the temperature is distributed unavoidably irregularly or inhomogeneously in the balloon. Therefore, the tissues in contact with the balloon cannot be uniformly heated.

SUMMARY OF THE INVENTION

Accordingly, it is an object of the present invention to solve those problems in the prior art and to provide a radiofrequency thermal balloon catheter capable of uniform heating of the tissues in contact with the balloon to achieve thermotherapy such as ablation or hyperthermia safely and properly for a diseased part.

According to the present invention, a radiofrequency thermal balloon catheter comprises a catheter consisting of an outer shaft and an inner shaft extended through the outer shaft so as to be slidable relative to the outer shaft. An inflatable balloon is capable of being inflated so as to be in contact with a target lesion and is provided between respective front end parts of the outer and the inner shaft. A radiofrequency electrode is used for radiofrequency energy supply in combination with a counter electrode, extended in a wall of the balloon or inside the balloon, the counter electrode being disposed at a predetermined position. A lead wire electrically connects to the radiofrequency electrode. A temperature sensor is capable of sensing the temperature of a liquid contained in the balloon and a temperature distribution uniformizing means uniformizes the temperature distribution in the liquid contained in the balloon.

The temperature distribution uniformizing means uniformizes the temperature distribution in the liquid contained in the balloon to prevent an irregular temperature distribution in the liquid contained in the balloon due to convection or the like, so that the target lesion in contact with the balloon can be uniformly heated by radiofrequency heating. Since the temperature distribution in the liquid contained in the balloon can be uniformized, temperature of the liquid measured by the temperature sensor can be made to coincide accurately with the temperature of the target lesion, and hence the temperature of the target lesion can be accurately controlled.

The temperature distribution uniformizing means may be a stirring means for stirring the liquid contained in the balloon. The stirring means stirs the liquid to make the temperature distribution in the liquid uniform.

The radio frequency thermal balloon catheter may further comprise a turning front sleeve put on a front end part of the inner shaft for turning about an axis of the catheter, a turning rear sleeve put on a front end part of the outer shaft for turning about the axis of the catheter, and a turning base sleeve holding the lead wire so that radiofrequency energy can be supplied to the lead wire and the lead wire can be turned. The radiofrequency electrode includes a plurality of electrode lines extended in parallel to each other between the turning front sleeve and the turning rear sleeve. The stirring means includes a rotative driving means for driving the radiofrequency electrode, the turning front sleeve, the turning rear sleeve, the lead wire and the turning base sleeve for turning.

The rotative driving means of the stirring means drives the radiofrequency electrode, the turning front sleeve, the turning rear sleeve, the lead wire and the turning base sleeve for turning to turn the radiofrequency electrode during radiofrequency energy supply. Thus, uniform radiofrequency energy supply can be achieved and the temperature distribution in the liquid can be uniformized by the stirring effect of the turning radiofrequency electrode.

The radiofrequency electrode may include a plurality of electrode lines connected to the turning front sleeve and the turning rear sleeve in parallel to each other. Thus the radiofrequency electrode can be easily formed and can be uniformly distributed in the balloon.

Preferably, the linearly extended electrode lines forming the radiofrequency electrode can be warped in an arcuate shape so as to extend along the inner surface of the balloon when the outer shaft and the inner shaft are moved axially relative to each other to inflate the balloon.

The liquid contained in the balloon can be efficiently stirred by turning the electrode lines of the radiofrequency electrode warped in the arcuate shape and a uniform radiofrequency electric field can be created.

The lead wire may be wound helically, and the rotative driving means may turn the lead wire to turn the radiofrequency electrode.

When the helically wound lead wire is turned in one direction, the helically wound lead wire is able to turn in the opposite direction by its own resilience to restore its natural shape when the rotative driving means stops turning the helically wound lead wire.

The rotative driving means may drive the turning front sleeve, the turning rear sleeve, the lead wire and the turning base sleeve for turning alternately in opposite directions and may change the direction of turning of the turning front sleeve, the turning rear sleeve, the lead wire and the turning base sleeve after turning the same by a predetermined number turns in each of the opposite directions. Thus, the radiofrequency electrode can be simply turned alternately in opposite directions to stir the liquid contained in the balloon with the radiofrequency electrode.

The stirring means may include a connecting pipe connected to the outer shaft, communicating with the balloon by means of a passage defined by the outer shaft and the inner shaft, and a vibration generating means for applying vibrations to a liquid filling up the connecting pipe and the passage.

The vibration generating means applies vibrations to the liquid filling up the connecting pipe and the passage, and the vibrations are propagated to the liquid contained in the balloon and stir the liquid contained in the balloon to uniformize the temperature distribution in the liquid contained in the balloon.

The vibration generating means may apply vibrations to the liquid filling up the connecting pipe and the passage such that eddies are produced in the liquid contained in the balloon.

Eddies produced in the liquid contained in the balloon enables the efficient uniformization of temperature distribution in the liquid contained in the balloon.

The temperature distribution uniformizing means is a circulating means for circulating the liquid in the balloon so that temperature distribution in the liquid contained in the balloon is uniformized.

Temperature distribution in the liquid contained in the balloon can be uniformized by circulating the liquid of a fixed temperature by the circulating means.

A part of the inner shaft extending in the balloon may be provided with a plurality of small nozzles, and the circulating means may include a liquid supply means capable of supplying the liquid into the inner shaft to jet the liquid through the small nozzles and of sucking the liquid jetted into the balloon through the passage defined by the outer and the inner shaft.

The liquid supply means is capable of jetting the liquid through the small nozzles of the inner shaft and of recovering the liquid through the passage defined by the outer and the inner shaft.

The radiofrequency electrode may be wound helically around a part of the inner shaft, extending in the balloon. Thus, the radiofrequency electrode can be easily disposed in the balloon for highly efficient radiofrequency heating.

The balloon may be formed of an antithrombogenic, heat-resistant, and elastic resin. The balloon satisfactorily meets all characteristics required of the balloon.

The predetermined position may be a position on a patient's body, and the counter electrode is attached to the patient's body.

The predetermined position may be a position in the wall of the balloon or inside the balloon.

The predetermined position may be a position neighboring the balloon.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENTS

Figure 1:
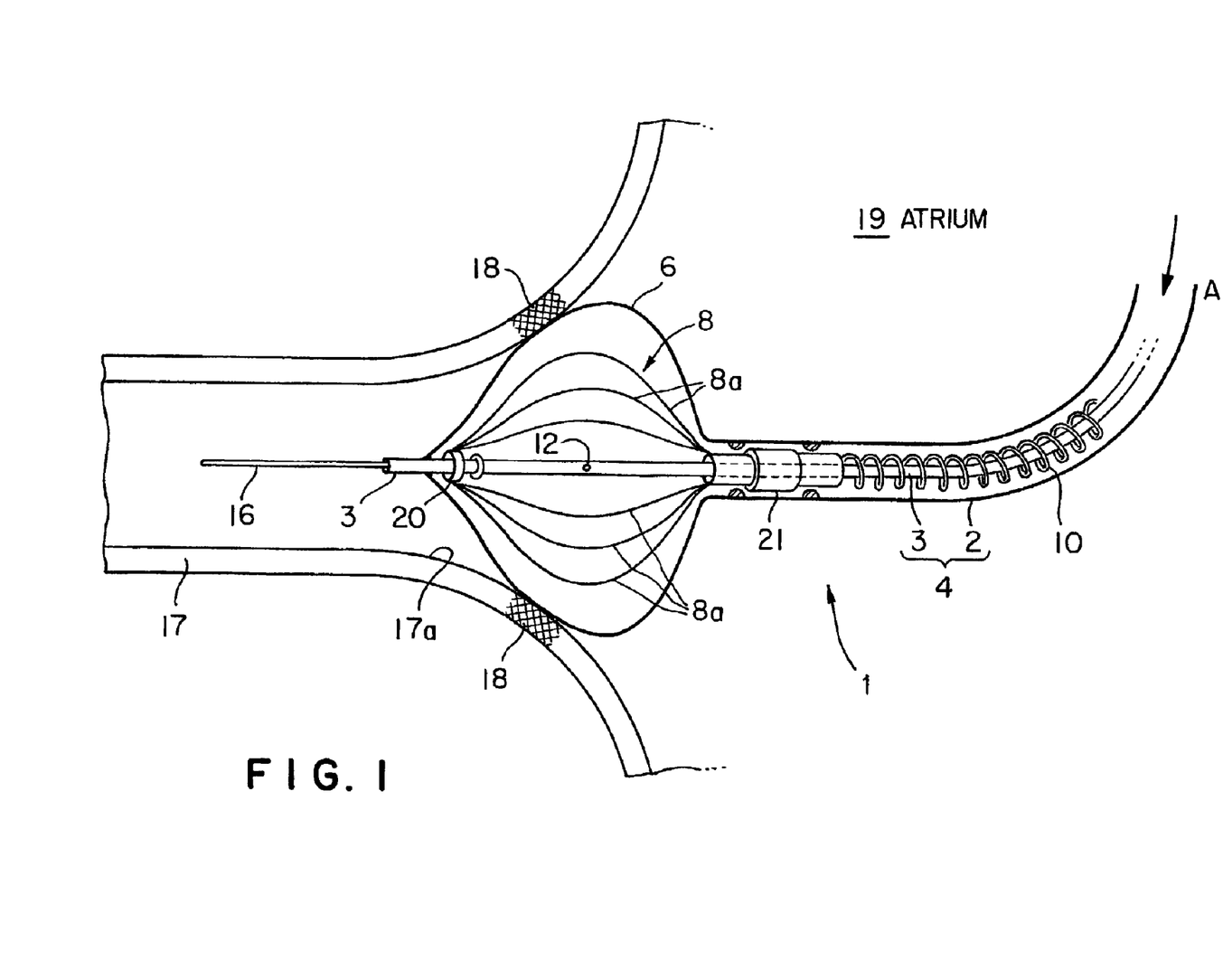
FIG. 1 is a schematic perspective view of a front part of radiofrequency thermal balloon catheter in a first embodiment according to the present invention.
Figure 2:
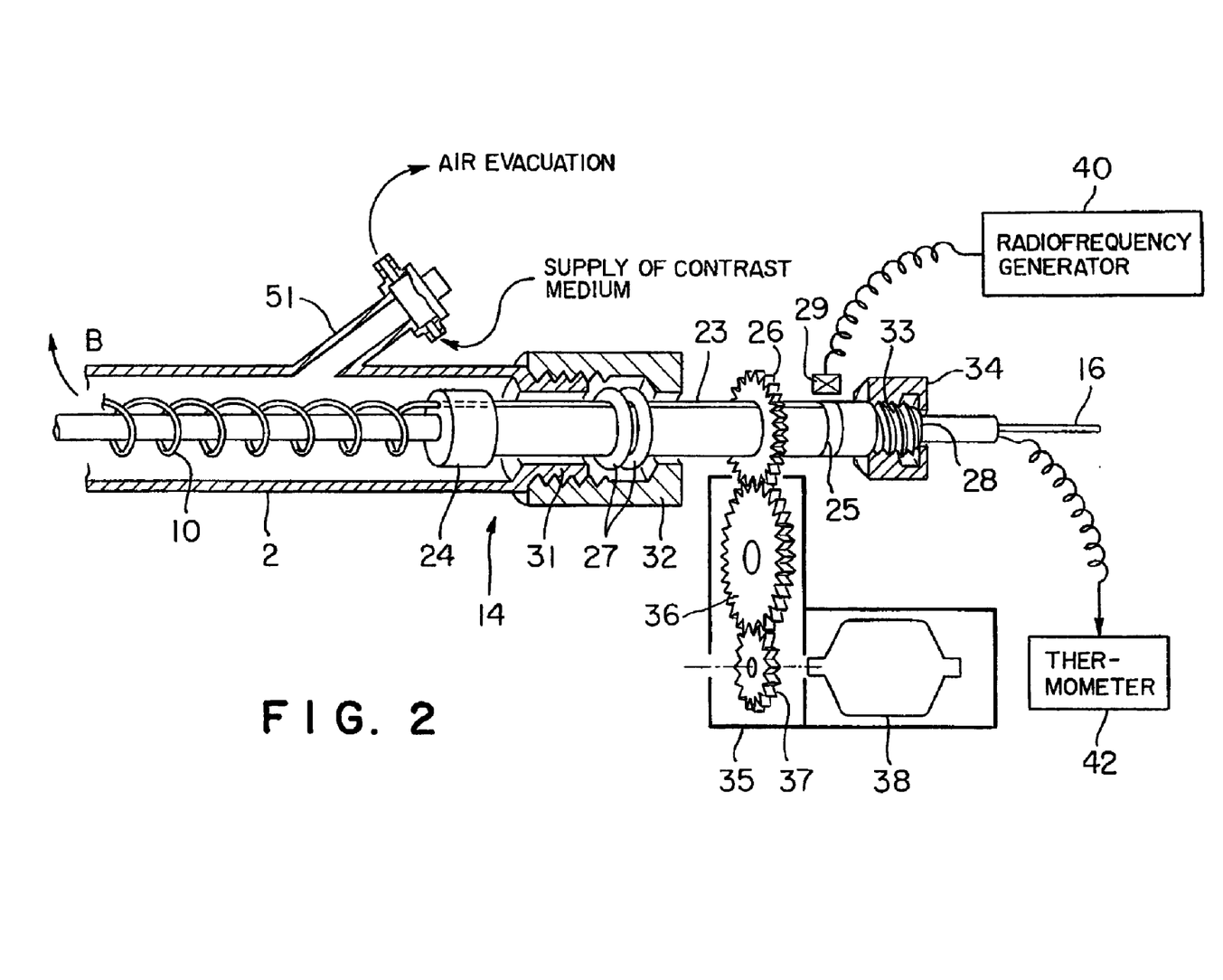
FIG. 2 is a schematic perspective view of a back part of the radiofrequency thermal balloon catheter continuous with the front part of the same shown in FIG. 1.

A radiofrequency thermal balloon catheter in a first embodiment according to the present invention will be described with reference to FIGS. 1 to 4. Referring to FIGS. 1 and 2, a radiofrequency thermal balloon catheter 1 includes a catheter 4 consisting of an outer shaft 2 and an inner shaft 3 extended in the outer shaft 2 so as to be slidable relative to the outer shaft 2, an inflatable balloon 6 capable of being inflated so as to be in contact with a target lesion and extended between respective end parts of the outer shaft 2 and the inner shaft 3, a radiofrequency electrode 8 disposed in the balloon 6, a lead wire 10 electrically connected to the radiofrequency electrode 8, a thermocouple 12 placed in the balloon 6 and capable of sensing temperature in the balloon 6, and a stirring device 14, i.e., a temperature distribution uniformizing means, for uniformizing temperature distribution in a liquid contained in the balloon 6. A guide wire 16 is extended through the inner shaft 3 substantially coaxially with the catheter 4. The guide wire 16 guides the catheter 4.

A turning front sleeve 20 is put on a front end part of the inner shaft 3 extending in the balloon 6 for turning about the axis of the catheter 4. A turning rear sleeve 21 is put on a front end part of the outer shaft 2 for turning about the axis of the catheter 4. The radiofrequency electrode 8 includes a plurality of electrode lines 8a extended in parallel to each other between the turning front sleeve 20 and the turning rear sleeve 21. The electrode lines 8a of the radiofrequency electrode 8 extend substantially linearly while the balloon 6 is deflated. When the balloon 6 is inflated by sliding the outer shaft 2 relative to the inner shaft 3, the electrode lines 8a are warped in an arcuate shape so as to extend along the inner surface of the balloon 6 as shown in FIG. 1.

A turning base sleeve 23 is put on the inner shaft 3 for turning about the axis of the catheter 4 at a position near the rear end of the outer shaft 2. The turning base sleeve 23 has a front end part provided with a ring 24, a rear end part provided with a contact ring 25, and a middle part provided with a gear 26. A brush 29 supported on a pantograph is kept in contact with the contact ring 25.

An external thread 31 is formed in a rear end part of the outer shaft 2. A nut 32 is engaged with the external thread 31. O rings 27 are put on the turning base sleeve 23 to seal the gap between the inner surface of the outer shaft 2 and the outer surface of the turning base sleeve 23 in a liquid-tight fashion. Thus the gap between the turning base sleeve 23 and the outer shaft 2, and the gap between the turning base sleeve 23 and the inner shaft 3 are sealed in a liquid-tight fashion. The inner shaft 3 extends through the turning front sleeve 20, the turning rear sleeve 21 and the turning base sleeve 23. An external thread 33 is formed in a rear end part of the turning base sleeve 23, and a nut 34 is engaged with the external thread 33. An O ring 28 is held between the rear end of the turning base sleeve 23 and the nut 34. The O ring 28 seals the gap between the outer surface of the inner shaft 3 and the inner surface of the turning base sleeve 23 in a liquid-tight fashion.

The lead wire 10 is coiled helically. The lead wire 10 has one end connected to the turning rear sleeve 21 and the other end connected to the contact ring 25. The brush 29 kept in contact with the contact ring 25 is connected electrically to a radiofrequency generator 40. Radiofrequency energy generated by the radiofrequency generator 40 is supplied through the lead wire 10 to the radiofrequency electrode 8. The radiofrequency generator applies a radiofrequency current of 13.56 MHz between the radiofrequency electrode 8 and a counter electrode 53 (FIG. 3) attached to the surface of the patient's body. For example, radiofrequency energy with an output of 100 to 200 W is supplied to the radiofrequency electrode 8 when the diameter of the balloon 6 is about 2.5 cm. When the radiofrequency current is applied between the radiofrequency electrode 8 and the counter electrode 53 attached to the surface of the patient's body, tissues 18 in contact with the balloon 6 are cauterized by capacitive type heating accompanying radiofrequency dielectric heating. The dielectric heating is generated around the electrode 8 inside the balloon 6 in proportion to the various dielectric constants. Consequently, the tissues 18 in contact with the balloon 6 are cauterized according to the principle of radiofrequency heating that heat is generated in touching parts of dielectric members respectively having different dielectric constants.

A reduction gear 35 having gears 36 and 37 and a motor 38 are disposed near the gear 26. The rotation of the output shaft of the motor 38 is transmitted through the gears 37 and 36 at a reduced speed to the gear 26. The motor 38 may be controlled such that the output shaft thereof rotates by a predetermined number of turns in one direction or may be controlled such that the output shaft thereof rotates alternately by two full turns in a clockwise direction and by two full turns in a counterclockwise direction.

The lead wire 10 is formed of a somewhat rigid material. When the motor 38 drives the turning base sleeve 23 fastened to the gear 26, the lead wire 10 connected to the ring 24 is turned and, consequently, the turning rear sleeve 21, the radiofrequency electrode 8 and the turning front sleeve 20 are turned.

When the motor 38 is controlled so as to turn the lead wire 10 by a predetermined number of turns in one direction, the lead wire 10 is turned in a direction opposite to a direction in which the lead wire 10 is wound helically. When the motor 38 is stopped after turning the lead wire 10 by a predetermined number of turns, the lead wire 10 turns automatically in the opposite direction to restore to its original shape. The radiofrequency electrode 8 can be turned alternately in opposite directions by alternately starting and stopping the motor 38. When the motor 38 is controlled such that the output shaft thereof rotates alternately by two full turns in a clockwise direction and by two full turns in a counterclockwise direction, the lead wire 10 is formed of a resilient material in a straight shape to turn the radiofrequency electrode 8 alternately in opposite directions.

The stirring device 14, i.e., a temperature distribution uniformizing means, includes the turning front sleeve 20, the turning rear sleeve 21, the turning base sleeve 23 and the motor 38 to turn the radiofrequency electrode 8. The lead wire 10 transmits the rotative driving motion of the motor 38 to the radiofrequency electrode 8, and transmits the radiofrequency energy generated by the radiofrequency generator 40 to the radiofrequency electrode 8. The stirring device 14 acts to eliminate local temperature differences generated in the balloon 6 and the stirring device 14 makes uniform the temperature distribution in the liquid inside the balloon 6.

A branch pipe 51 is connected to a rear end part of the outer shaft 2. The branch pipe 51 is provided with an air vent pipe and a contrast medium supply pipe. The air vent pipe of the branch pipe 51 is opened to evacuate the balloon 6, and then the contrast medium supply pipe of the same is opened to supply a liquid, such as a physiological saline solution, into the balloon 6 to inflate the balloon 6.

The inner shaft 3 is provided with two lumens, i.e., first and second lumens. The first lumen is used as a space for extending the guide wire 16 and as a passage for the liquid. The second lumen is used as a space for extending conductors for transmitting a signal provided by the thermocouple 12 attached to a middle part of an exposed segment of the inner shaft 3.

The temperature of the liquid contained in the balloon 6 is measured by the thermocouple 12 attached to the inner shaft 3. The conductors of the thermocouple 12 are extended through the second lumen of the inner shaft 3 and are connected to a thermometer 42. The thermometer 42 indicates the temperature of the liquid contained in the balloon 6.

The balloon 6 is formed of a heat-resistant, elastic, antithrombogenic resin. In an inflated state, the balloon 6 has a shape resembling an onion as shown in FIG. 1.

The radiofrequency electrode 8 includes the plurality of electrode lines 8a. The number of the electrode lines 8a is in the range of several to several tens. When the inner shaft 3 is moved axially relative to the outer shaft 2 to reduce the interval between the turning front sleeve 20 and the turning rear sleeve 21, the substantially linear electrode lines 8a are warped in an arcuate shape, so that the radiofrequency electrode 8 assumes a shape generally resembling a basket or an onion. If the electrode lines 8a are formed of a shape memory alloy, the electrode lines 8a are able to change their shape accurately between the substantially linear shape and the arcuate shape. Front and rear end parts of the electrode lines 8a are coated with a resin to prevent the excessive radiofrequency heating of the front and rear end parts of the electrode lines 8a.

Figure 3:
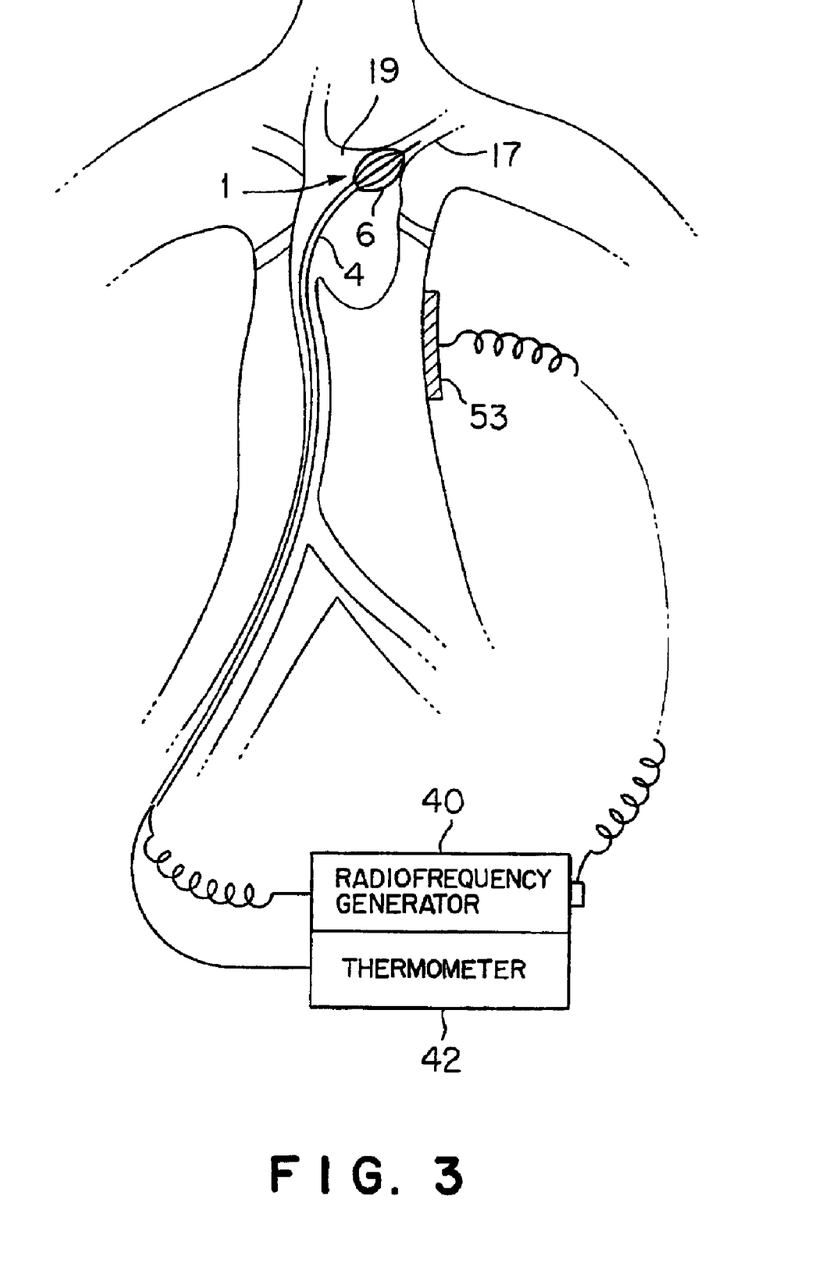
FIG. 3 is a schematic view of assistance in explaining the operation of the radiofrequency thermal balloon catheter as applied to electrical isolation of the pulmonary vein for the treatment of atrial fibrillation.

The radiofrequency generator 40 supplies power of a radiofrequency on the order of megahertz, such as 13.56 MHz, to the radiofrequency electrode 8. Thus, heat is generated by capacitive radiofrequency heating in a part of the patient's body between the radiofrequency electrode 8 and the counter electrode 53 attached to the surface of the patient's back as shown in FIG. 3.

The radiofrequency electrode 8 is connected to the contact ring 25 of the turning base sleeve 23 by the helical lead wire 10. The brush 29 supported on the pantograph and connected to the radiofrequency generator 40 is kept in contact with the contact ring 25 to supply radiofrequency energy to the radio frequency electrode 8. The radio frequency electrode 8 is turned to create a further uniform radiofrequency electric field around the radiofrequency electrode 8.

The reduction gear 35 reduces an input speed, i.e., the rotating speed of the output shaft of the motor 38, to a lower output speed. The rotative force of the motor 38 is transmitted through the reduction gear 35 and the gear 26 to the turning base sleeve 23. The rotation of the turning base sleeve 23 is transmitted to the turning rear sleeve 21 by the lead wire 10 to turn the electrode lines 8a in the balloon 6. Consequently, the liquid filling up the inflated balloon 6 is stirred by the electrode lines 8a to prevent an irregular temperature distribution due to convection and to uniformize temperature distribution in the liquid filling up the balloon 6. Thus, the temperature of the liquid in a central region in the balloon 6, the temperature of the liquid in the vicinity of the wall of the balloon 6 and the temperature of the tissues 18 in contact with the balloon 6can be equalized. Therefore, the temperature of the liquid in the central region in the balloon 6 measured by the thermocouple 12 and indicated by the thermometer 42 represents the temperature of the tissues 18 in contact with the balloon 6 accurately.

The temperature of the liquid is measured by the thermocouple 12 disposed in the middle part of exposed segment of the inner shaft 3 while the radiofrequency energy is supplied to the radiofrequency electrode 8, and the output of the radiofrequency generator 40 is controlled in a feedback control mode so that the liquid filling up the balloon 6 is heated at an optimum temperature. Consequently, the tissues 18 in contact with the balloon 6 can be heated at an optimum temperature.

The turning basketlike radiofrequency electrode 8 creates a more uniform radiofrequency electric field, and stirs the liquid filling up the balloon 6. Thus, temperature distribution in the liquid is uniformized and the tissues 18 in contact with the balloon 6 can be heated accurately at a desired temperature.

The operation of the radiofrequency thermal balloon catheter 1 as applied to the electrical isolation of the pulmonary vein for the treatment of atrial fibrillation will be described.

Figure 4A:
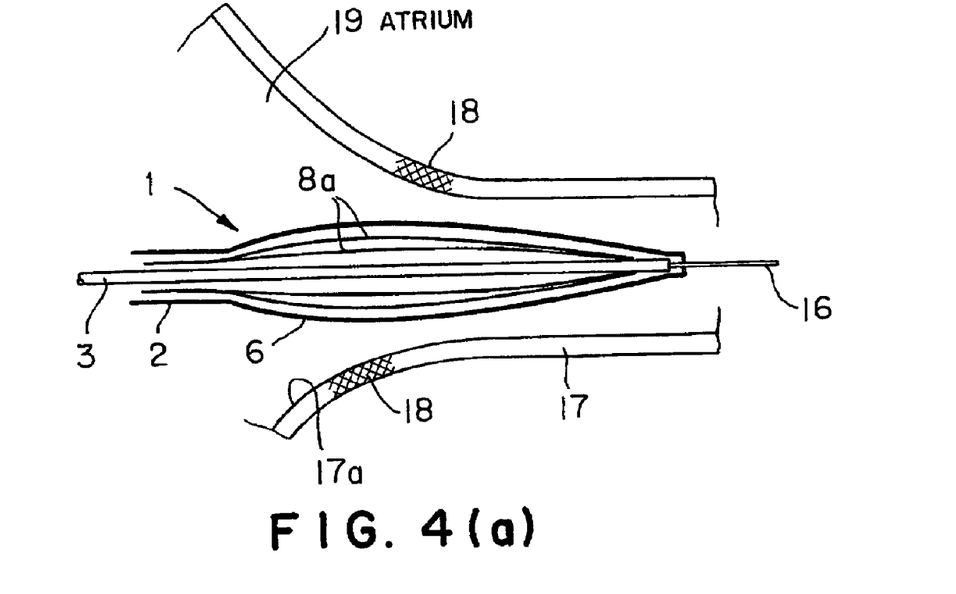
FIGS. 4(a) and 4(b) are schematic views of a balloon catheter in a state where the balloon is deflated for insertion in the pulmonary vein and in a state where the balloon is inflated to contact with a target lesion, respectively.
Figure 4B:
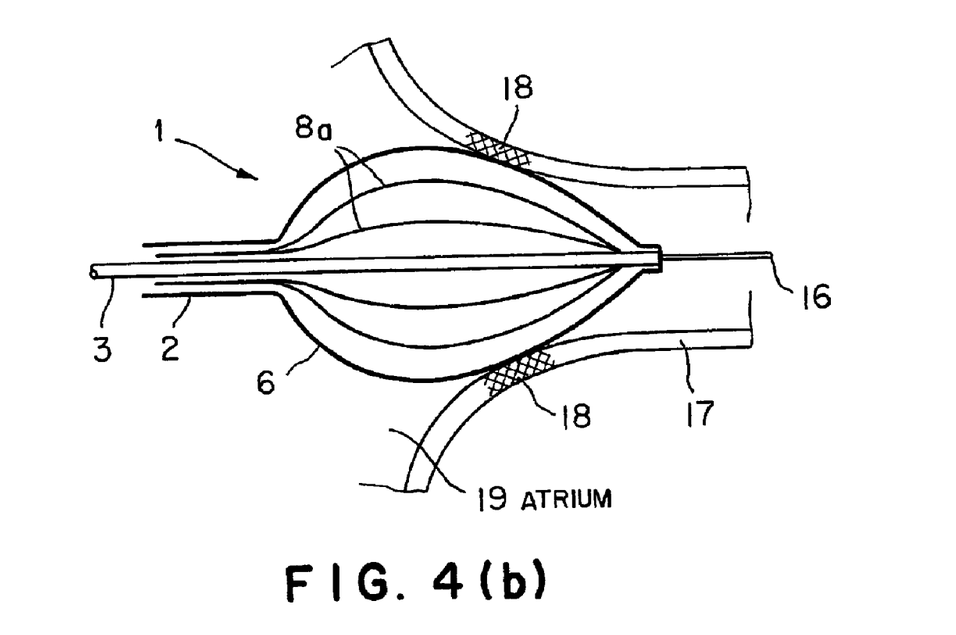

FIG. 3 is a view of assistance in explaining an operation for cauterizing the tissues 18 of the atrium 19 around the ostium 17a (FIG. 4(a)) of the pulmonary vein 17. A cycle of supplying a physiological saline solution through the branch pipe 51 of the outer shaft 2 into the balloon 6 and sucking the physiological saline solution out of the balloon 6 is repeated several times to purge the balloon 6 of air. As shown in FIG. 4(a), the balloon 6 is deflated and the inner shaft 3 is fully projected from the outer shaft 2 such that the distance between the turning front sleeve 20 and the turning rear sleeve 21 is increased to a limit and the electrode lines 8a of the radiofrequency electrode 8 extend substantially linearly before inserting the radiofrequency thermal balloon catheter 1 in the pulmonary vein 17. In this state, the diameter of the balloon 6 is reduced to its minimum. Then, the balloon 6 is inserted in the pulmonary vein 17. The radiofrequency thermal balloon catheter 1 is operated to locate the balloon 6 near the target tissues 18. Then, as shown in FIG. 4(b), the inner shaft 3 is retracted, supplying the contrast medium and the physiological saline solution through the branch pipe 51 into the balloon 6 to inflate the balloon 6. Since the turning front sleeve 20 is moved toward the turning rear sleeve 21, the electrode lines 8a are warped in an arcuate shape. Thus, the radiofrequency electrode 8 is expanded in the shape of a basket in the balloon 6. The radiofrequency thermal balloon catheter 1 is operated minutely to bring the balloon 6 into contact with the target tissues 18.

Then, the motor 38 is started to drive the turning base sleeve 23 for turning through the reduction gear 35. The turning motion of the turning base sleeve 23 is transmitted to the turning rear sleeve 21 by the helical lead wire 10 extended through the catheter 4. Consequently, the radiofrequency electrode 8 expanded in the shape of a basket in the balloon 6 is turned to stir the liquid filling up the balloon 6.

Subsequently, the radiofrequency generator 40 applies a radiofrequency current of, for example, 13.56 MHz between the counter electrode 53 attached to the patient's back, and the contact ring 25 connected to the radiofrequency electrode 8 expanded in the shape of a basket of the radiofrequency thermal balloon catheter 1. A radiofrequency current flows through the brush 29 in contact with the contact ring 25. Consequently, the balloon 6 and the tissues 18 in contact with the balloon 6 are heated by radiofrequency capacitive type heating accompanying radiofrequency dielectric heating. Although the temperature of an upper region in the balloon 6 is higher than that of a lower region in the balloon 6 due 30 to convection if the liquid contained in the balloon 6 is not stirred, the temperature distribution in the liquid contained in the balloon 6 is uniform because the liquid is stirred by the turning radiofrequency electrode 8 expanded in the shape of a basket. The tissues 18 are heated irregularly if the radiofrequency electrode 8 is misaligned with the balloon 6 and is fixedly held in the balloon 6. Since the radiofrequency electrode 8 is turned, a uniform radiofrequency electric field is created around the radiofrequency electrode 8, and the balloon 6 and the tissues 18 are heated uniformly by radiofrequency heating.

Parts of the balloon 6 near the turning sleeves 20 and 21 around which the electrode lines 8a are gathered have a tendency to be overheated. Such overheating can be avoided by forming the turning sleeves 20 and 21 of a material having a small dielectric constant, such as a resin or a ceramic material, by coating parts of the electrode lines 8a with a resin and/or by circulating cooling water through the inner shaft 3.

Thus, the pulmonary vein 17 can be electrically isolated by cauterizing the tissues 18 of an annular part of the atrium 19 around the pulmonary vein 17 to safely treat the patient with atrial fibrillation.

Figure 5:
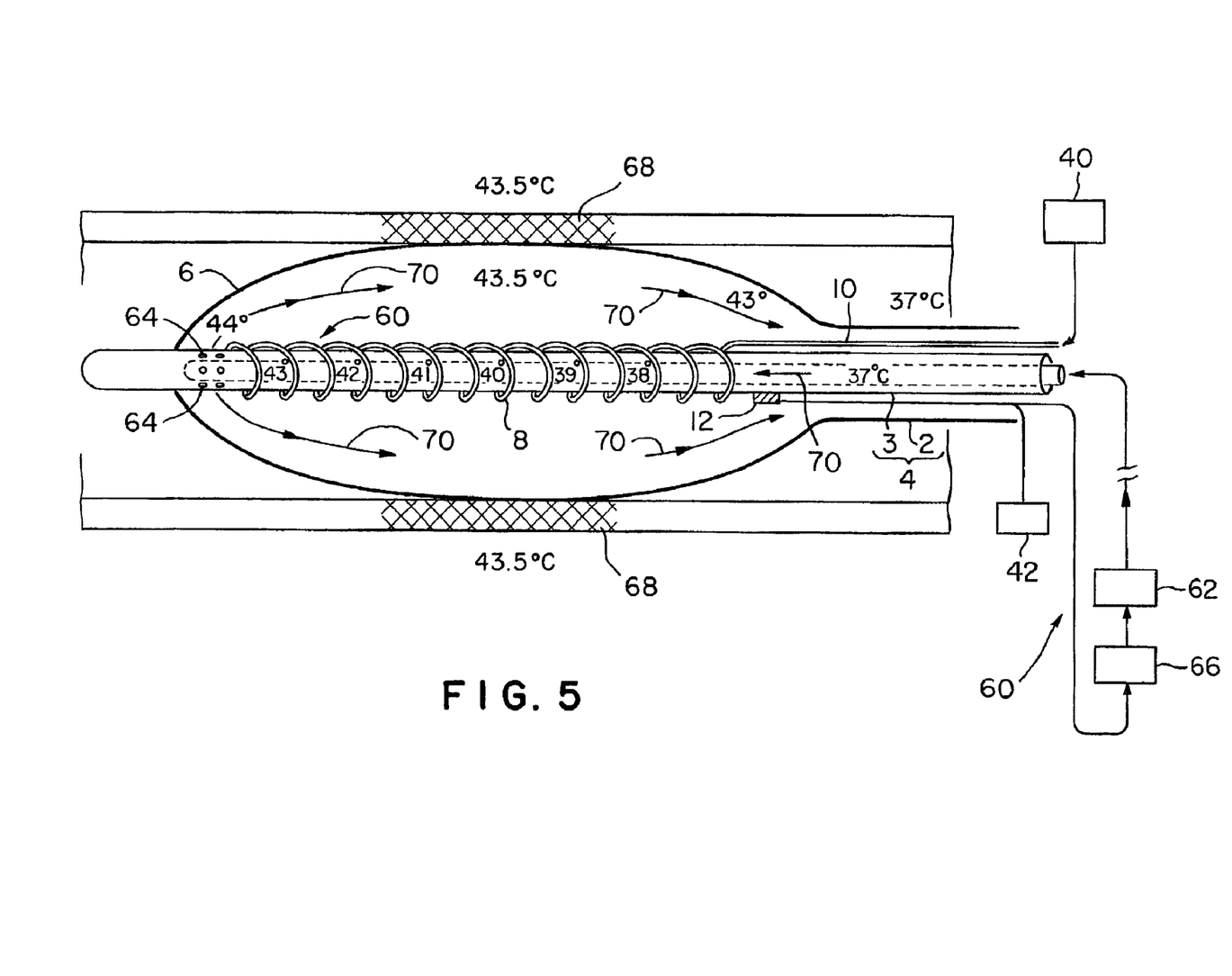
FIG. 5 is a schematic perspective view of a radiofrequency thermal balloon catheter in a second embodiment according to the present invention.

A radiofrequency thermal balloon catheter 1 in a second embodiment according to the present invention will be described hereinafter. The radiofrequency thermal balloon catheter 1 includes a circulating system 60 for circulating a liquid contained in a balloon 6 to uniformize temperature distribution in the liquid. A part of an inner shaft 3 extending in the balloon 6 is provided with a plurality of small nozzles 64. The circulating system 60 includes a temperature controller 66 for keeping a liquid to be supplied into the inner shaft 3 at, for example, 37° C., and a liquid supply device 62 capable of supplying the liquid of a predetermined temperature controlled by the temperature controller 66 into the inner shaft 3 and of sucking the liquid jetted through the small nozzles 64 into the balloon 6 through an annular space between the inner shaft 3 and an outer shaft 2. When inflated, the balloon 6 has an ellipsoidal shape. A radiofrequency electrode 8 is wound helically around the part of the inner shaft 3 extending in the balloon 6. The radiofrequency electrode 8 is connected to a radiofrequency generator 40 by a lead wire 10. The temperature of the liquid contained in the balloon 6 is measured with a thermocouple 12 and is monitored by a method similar to that mentioned in the description of the first embodiment, and radiofrequency energy to be supplied to the radiofrequency electrode 8 is controlled according to the measured temperature.

As shown in FIG. 5, a circulating liquid 70 controlled at, for example, 37° C. by the temperature controller 66 is heated at 44° C. while the same is flowing through the part of the inner shaft 3 extending in the balloon 6 and is jetted through the small nozzles 64 into the balloon 6. The temperature of the circulating liquid 70 jetted into the balloon 6 drops to 43.5° C. and drops further to 43° C. when the circulating liquid 70 reaches the front end of the outer shaft 2. The circulating liquid 70 is thus circulated by the circulating system 60 to keep the liquid contained in the balloon 6 uniformly at about 43.5° C.

Figure 7:
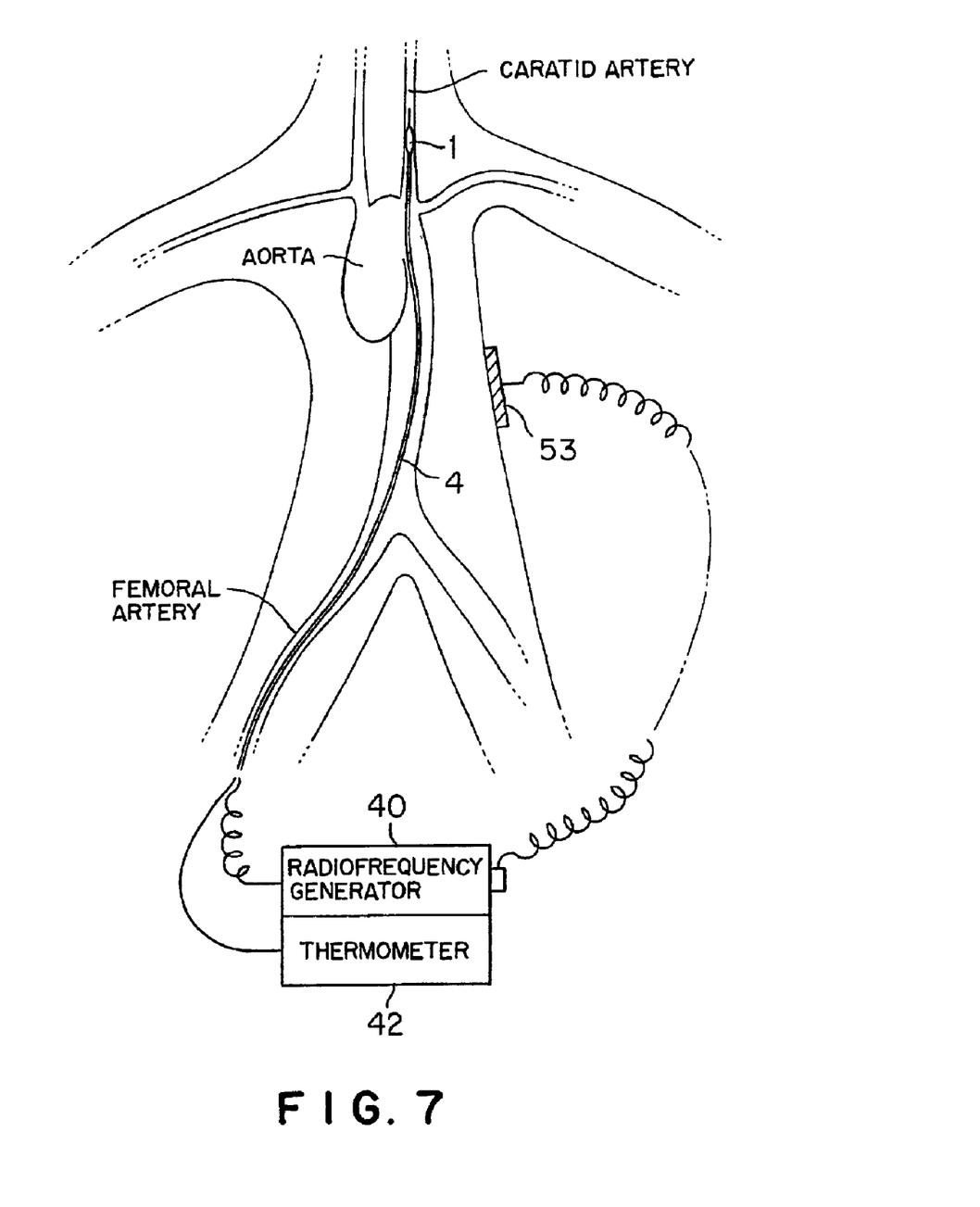
FIG. 7 is a schematic view of assistance in explaining the use of a thermal balloon catheter for the treatment of arterial sclerosis.

The radiofrequency thermal balloon catheter 1 shown in FIG. 5 will be described as applied to the medical treatment of an arteriosclerotic part as shown in FIG. 7.

Figure 6A:
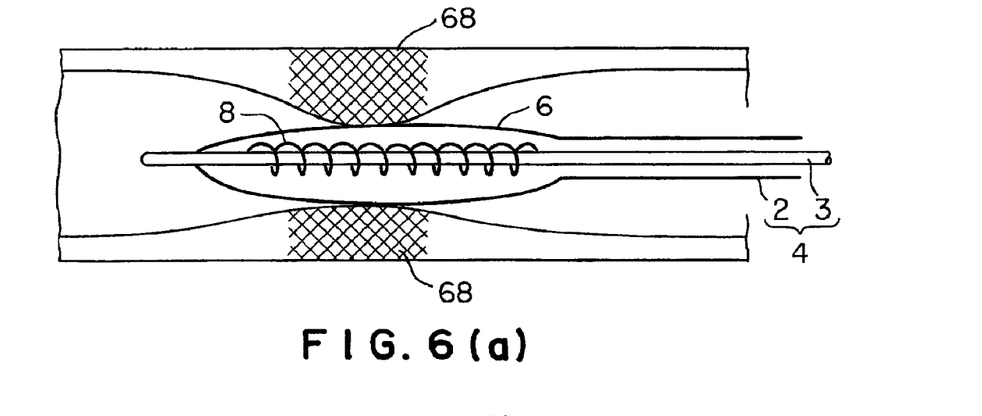
FIGS. 6(a) and 6(b) are schematic views of the radiofrequency thermal balloon catheter shown in FIG. 5 in a state where a balloon is deflated for insertion in the femoral artery and a state where the balloon is inflated to contact with the vicinity of a target tissue, respectively.
Figure 6B:
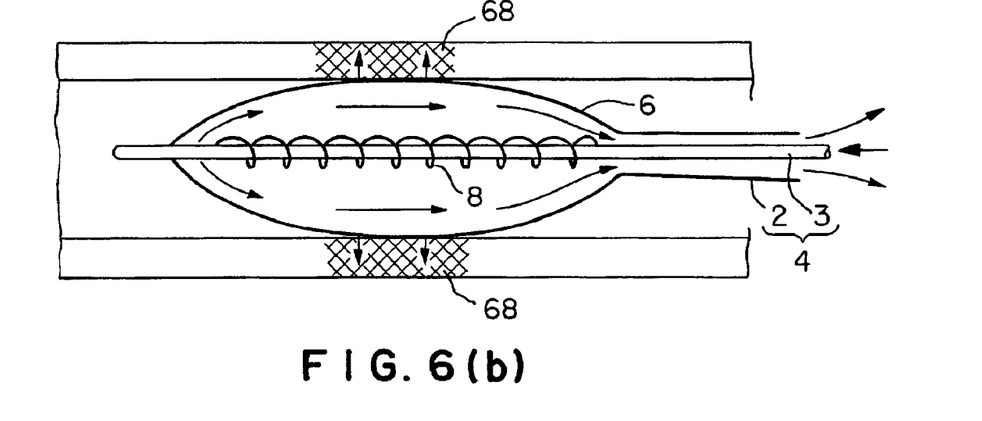

The balloon 6 of the radiofrequency thermal balloon catheter 1 is deflated and the radiofrequency thermal balloon catheter 1 is inserted through the femoral artery in a diseased part 68 of the carotid artery as shown in FIG. 6(a). Then, a contrast medium and a physiological saline solution are supplied through a branch pipe 51 attached to the outer shaft 2 into the balloon 6. Consequently, the balloon 6 is inflated to expand a stricture in the diseased part 68 as shown in FIG. 6(b). In this state, the application of a radiofrequency voltage of 13.56 MHz across the radiofrequency electrode 8 and a counter electrode 53 attached to the patient's back is started.

The circulating system 60 supplies the circulating liquid 70 of, for example 37° C. by pressure into the lumen of the inner shaft 3. The circulating liquid 70 heated by radiofrequency heating is jetted through the small nozzles 64 into the balloon 6. The circulating liquid 70 flows through the balloon 6, uniformizing temperature distribution in the balloon 6, and is discharged through the lumen of the outer shaft 2. When the balloon 6 is maintained at 43.5° C. for 20 min or longer, the inflammatory cells or the proliferous smooth muscle cells in the atherosclerotic lesion part 68 of the carotid artery undergo apotosis and the atherosclerotic lesion part 68 of the carotid artery stabilizes. Then, the balloon 6 is deflated and the radiofrequency thermal balloon catheter 1 is extracted from the femoral artery.

The radiofrequency thermal balloon catheter 1 is capable of uniformly heating the tissues of the diseased part 68 at an optimum temperature. Thus, the atherosclerotic lesion part 68 of the carotid artery can be stabilized through the apotosis of the inflammatory cells or the proliferous smooth muscle cells macrophages, i.e., labile factors, by heating the atherosclerotic lesion part 68 of the carotid artery at 43.5° C. for 20 min or longer without affecting normal tissues, such as endothelia.

The radiofrequency thermal balloon catheter 1 can be applied to hyperthermia for cancer. It is proved that cancer cells can be controlled or eradicated by heating the same at 43.5° C. for 20 min or longer.

Figure 8:
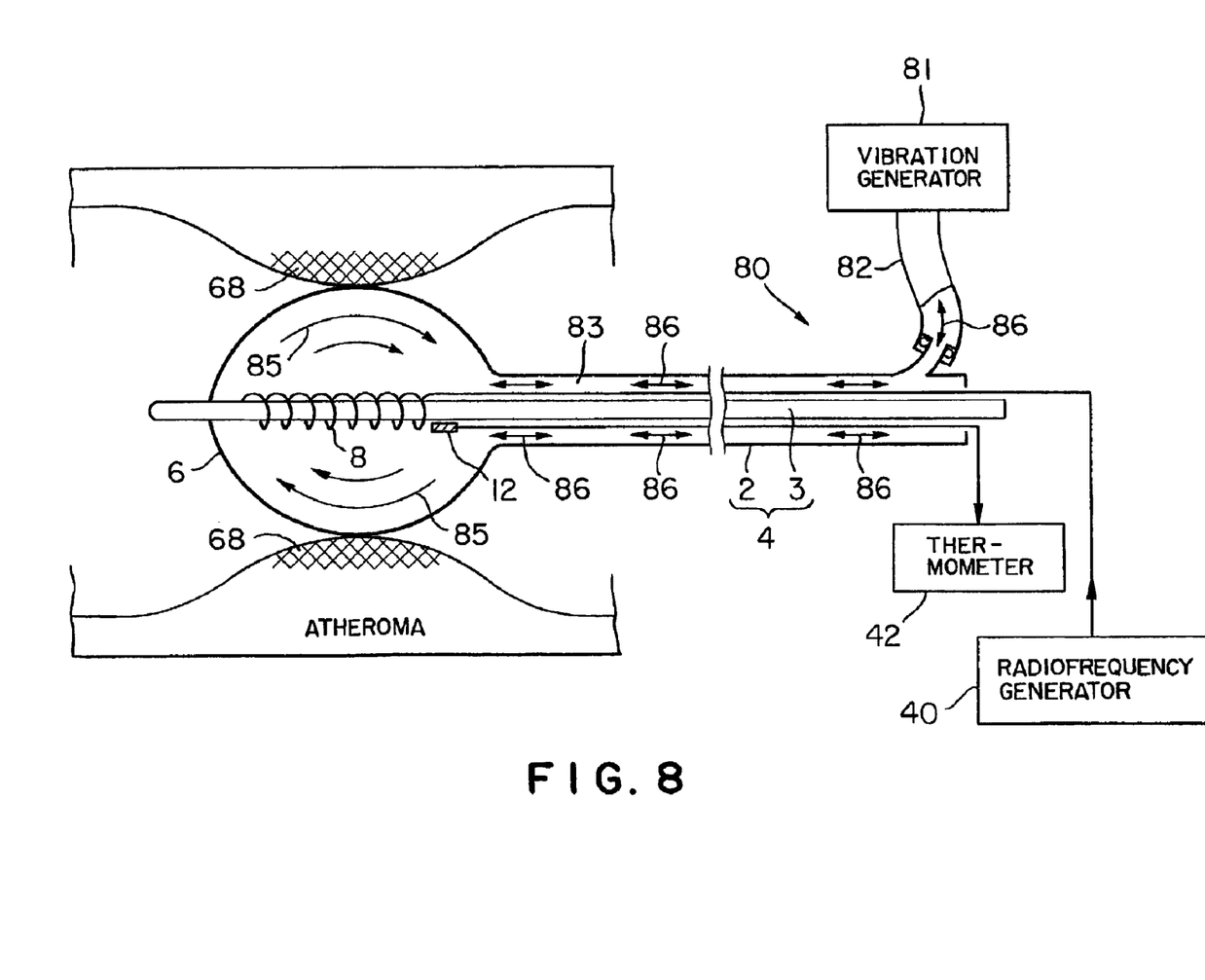
FIG. 8 is a partial view of a radiofrequency thermal balloon catheter in a third embodiment according to the present invention.

Referring to FIG. 8 showing a radiofrequency thermal balloon catheter 1 in a third embodiment according to the present invention, the radiofrequency thermal balloon catheter 1 includes a balloon 6 and a stirring device 80 for stirring a liquid contained in the balloon 6 to uniformize temperature distribution in the liquid.

The stirring device 80 includes a connecting pipe 82 connected to an outer shaft 2 so as to open into an annular passage 83 defined by the outer shaft 2 and an inner shaft 3 extended through the outer shaft 2, and a vibration generator 81, such as a vibration-generating diaphragmatic pump, to apply vibrations to a liquid filling up the annular passage 83. The connecting pipe 82 communicates with the balloon 6 by means of the annular passage 83. Vibrations 86 of, for example, about 1 Hz generated by the vibration generator 81 propagate through the liquid filling up the connecting pipe 82 and the annular passage 83. Consequently, eddies 85 are produced in the liquid contained in the balloon 6 due to the interaction between the oscillated liquid and the gravity. The eddies stir the liquid through going indefinite directions, so that temperature distribution in the liquid contained in the balloon 6 is uniformized. Thus, atheroma formed in the tissues 68 can be heated homogeneously at an optimum temperature.

A radiofrequency electrode 8 helically wound around the inner shaft 3, similar to the radiofrequency electrode 8 shown in FIG. 5, is used for radiofrequency heating.

Satisfactory eddies can be produced in the liquid contained in the balloon 6 by the vibrations 86 generated by the vibration generator 81 when the balloon 6 is formed of a properly elastic material.

As apparent from the foregoing description, the radiofrequency thermal balloon catheter of the present invention is capable of uniformly heating tissues in contact with the balloon at an optimum temperature by radiofrequency heating and of safely forming a penetrating three-dimensional necrotic layer without causing ulceration due to the thrombus formation or the charring of tissues. Therefore, it is possible to achieve safely and surely the treatment of the arrhythmias such as atrial fibrillation triggered by an extrasystole from the pulmonary vein and its ostium through isolation of the pulmonary veins.

Since the tissues can be uniformly heated at an optimum temperature, an arteriosclerotic part can be stabilized by heating the arteriosclerotic part at a predetermined temperature to make the inflammatory cells or the proliferative smooth muscle cells which are the factors of instability, undergo apotosis without affecting normal tissues, such as endothelium.

Although the invention has been described in its preferred embodiment with a certain degree of particularity, obviously many changes and variations are possible therein.

For example, it is described in its preferred embodiment that the counter electrode 53 is attached to the surface of the patient's body. However, the position, where the counter electrode 53 is disposed, is not limited to the surface of the patient's body. The counter electrode 53 may be disposed at a position in the wall of the balloon or inside the balloon, or the counter electrode 53 may be disposed at a position neighboring the balloon.

It is therefore to be understood that the present invention may be practiced otherwise than as specifically described herein without departing from the scope and spirit thereof.

What is claimed is:

1. A radio-frequency thermal balloon catheter, comprising:

a catheter comprising an outer shaft and an inner shaft extending through said outer shaft so as to be slidable relative to said outer shaft;

an inflatable balloon capable of being inflated so as to be in contact with a target lesion, said balloon being provided between a front end part of said outer shaft and a front end part of said inner shaft;

a counter electrode and a radio-frequency electrode to be used for supplying radio-frequency energy in combination with said counter electrode;

a lead wire electrically connected to said radio-frequency electrode;

a temperature sensor capable of sensing temperature of a liquid in said balloon;

a turning front sleeve on said front end part of said inner shaft operable to turn about an axis of said catheter;

a turning rear sleeve on said front end part of said outer shaft operable to turn about the axis of said catheter;

a turning base sleeve holding said lead wire such that radio-frequency energy can be supplied to said lead wire and so that said lead wire can be turned;

wherein said radio-frequency electrode includes a plurality of electrode lines between said turning front sleeve and said turning rear sleeve; and a stirring device comprising a rotational drive operable to turn said radio-frequency electrode, said turning front sleeve, said turning rear sleeve, said lead wire and said turning base, whereby a temperature distribution of liquid in said balloon can be uniformized.

2. The radio-frequency thermal balloon catheter of claim 1, wherein said plurality of electrode lines of said radio-frequency electrode are connected to said turning front sleeve and said turning rear sleeve in parallel to each other.

3. The radio-frequency thermal balloon catheter of claim 2, wherein said plurality of electrode lines can be warped in to an arcuate shape so as to extend along an inner surface of said balloon when said outer shaft and said inner shaft are moved axially relative to each other to inflate said balloon.

4. The radio-frequency thermal balloon catheter of claim 1, wherein said lead wire is helically wound and said rotational drive turns said lead wire to turn said radio-frequency electrode.

5. The radio-frequency thermal balloon catheter of claim 1, wherein said rotational drive is operable to alternately turn in opposite directions so as to change a direction of turning of said turning front sleeve, said turning rear sleeve, said lead wire and said turning base sleeve after turning a predetermined number of turns in the same direction of each of the opposite directions.

6. A radio-frequency thermal balloon catheter, comprising:
   a catheter comprising an outer shaft and an inner shaft extending through said outer shaft so as to be slidable relative to said outer shaft;
   an inflatable balloon capable of being inflated so as to be in contact with a target lesion, said balloon being provided between a front end part of said outer shaft and a front end part of said inner shaft;
   a counter electrode and a radio-frequency electrode to be used for supplying radio-frequency energy in combination with said counter electrode such that liquid contained in said balloon can be heated by radio-frequency energy supplied by said radio-frequency electrode and said counter electrode, said counter electrode being located at a predetermined position;
   a lead wire electrically connected to said radio-frequency electrode;
   a temperature sensor capable of sensing temperature of a liquid in said balloon; and
   a stirring device operable to stir liquid contained in said balloon to uniformize a temperature distribution of the liquid, said stirring device comprising:
     a connecting pipe connected with said outer shaft and communicating with said balloon by a passage defined by said outer shaft and said inner shaft, and
     a vibration generator operable to apply vibrations to liquid in said connecting pipe and said passage.

7. The radio-frequency thermal balloon catheter of claim 6, wherein said vibration generator is operable to apply vibration to the liquid in said connecting pipe and said passage such that eddies are produced in the liquid contained in said balloon.

8. The radio-frequency thermal balloon catheter of claim 7, wherein said radio-frequency electrode is helically wound around a part of said inner shaft inside said balloon.

9. The radio-frequency thermal balloon catheter of claim 6, wherein said radio-frequency electrode is helically wound around a part of said inner shaft inside said balloon.

10. The radio-frequency thermal balloon catheter of claim 6, wherein said balloon is formed of an antithrombogenic, heat-resistant and elastic resin.

11. The radio-frequency thermal balloon catheter of claim 6, wherein said predetermined position is a position on a patient's body and said counter electrode is attached to the patient's body.

12. The radio-frequency thermal balloon catheter of claim 6, wherein said predetermined position is a position in a wall of said balloon or inside said balloon.

13. The radio-frequency thermal balloon catheter of claim 6, wherein said predetermined position is a position neighboring said balloon.

14. A radio-frequency thermal balloon catheter, comprising:
   a catheter comprising an outer shaft and an inner shaft extending through said outer shaft so as to be slidable relative to said outer shaft, a passage being defined by said outer shaft and said inner shaft;
   an inflatable balloon capable of being inflated so as to be in contact with a target lesion, said balloon being provided between a front end part of said outer shaft and a front end part of said inner shaft;
   a counter electrode and a radio-frequency electrode to be used for supplying radio-frequency energy in combination with said counter electrode;
   a lead wire electrically connected to said radio-frequency electrode;
   a temperature sensor capable of sensing temperature of a liquid in said balloon; and
   a circulating system operable to circulate liquid in said balloon to uniformize a temperature distribution of the liquid, said circulating system comprising:
     a plurality of small nozzles in a part of said inner shaft in said balloon, and
     a liquid supply operable to supply liquid into said inner shaft so as to jet the liquid through said small nozzles and to suction the liquid jetted into said balloon through said passage defined by said outer shaft and said inner shaft.

15. The radio-frequency thermal balloon catheter of claim 14, wherein said radio-frequency electrode is helically wound around a part of said inner shaft inside said balloon.

* * * * *